(12) United States Patent
Gal et al.

(10) Patent No.: US 7,362,516 B2
(45) Date of Patent: Apr. 22, 2008

(54) OPTICAL LENS PROVIDING OMNI-DIRECTIONAL COVERAGE AND ILLUMINATION

(75) Inventors: Ehud Gal, Reut (IL); Gil Graisman, Reut (IL); Gennadiy Liteyga, Ashkelon (IL)

(73) Assignees: O.D.F. Optronics, Ltd., Tel Aviv (IL); O.D.F. Medical Ltd., Tel Aviv (IL)

( * ) Notice: Subject to any disclaimer, the term of this patent is extended or adjusted under 35 U.S.C. 154(b) by 0 days.

(21) Appl. No.: 10/521,127

(22) PCT Filed: Jul. 3, 2003

(86) PCT No.: PCT/IL03/00558

§ 371 (c)(1),
(2), (4) Date: Nov. 7, 2005

(87) PCT Pub. No.: WO2004/008185

PCT Pub. Date: Jan. 22, 2004

(65) Prior Publication Data

US 2006/0164733 A1   Jul. 27, 2006

(30) Foreign Application Priority Data

Jul. 15, 2002   (IL) ..................................... 150746

(51) Int. Cl.
*G02B 13/06* (2006.01)
*G02B 17/00* (2006.01)

(52) U.S. Cl. ...................... 359/725; 359/726
(58) Field of Classification Search ................ 359/725; 348/36, 38–39
See application file for complete search history.

(56) References Cited

U.S. PATENT DOCUMENTS

| 4,566,763 A | * | 1/1986 | Greguss ...................... 359/725 |
| 4,899,277 A | | 2/1990 | Iizuka et al. |
| 5,282,016 A | | 1/1994 | Shen et al. |
| 5,473,474 A | * | 12/1995 | Powell ........................ 359/725 |
| 5,774,569 A | | 6/1998 | Waldenmaier |
| 5,790,182 A | | 8/1998 | St. Hilaire |
| 5,854,713 A | | 12/1998 | Kuroda et al. |
| 6,028,719 A | | 2/2000 | Beckstead et al. |
| 6,115,193 A | * | 9/2000 | Shu ............................ 359/725 |
| 6,157,018 A | | 12/2000 | Ishiguro et al. |

(Continued)

FOREIGN PATENT DOCUMENTS

WO    WO 02/059676 A1    8/2002

(Continued)

*Primary Examiner*—Jordan M. Schwartz
(74) *Attorney, Agent, or Firm*—Clifford J. Mass

(57) ABSTRACT

The invention presents a wide-angle imaging assembly which comprises a main lens produced from an aspheric optical block. The aspheric optical block comprises a vertical axis of symmetry; a transparent upper surface, at least part of which is capable of reflecting rays that impinge upon it from the interior of the optical block; a transparent perimeter surface; and a transparent lower surface. The optical block is fabricated from material selected to enable optical transmittance of a specific spectral range. Light rays in the specific spectral range originating in a first scene, having a 360 degrees panoramic perimeter, are refracted by the transparent perimeter surface, enter the optical block, are then reflected by the upper surface towards the transparent lower surface, where they are then refracted by the transparent lower surface, and exit through it.

7 Claims, 12 Drawing Sheets

U.S. PATENT DOCUMENTS

| | | |
|---|---|---|
| 6,222,683 B1 | 4/2001 | Hoogland et al. |
| 6,341,044 B1 | 1/2002 | Driscoll, Jr. et al. |
| 6,388,820 B1 | 5/2002 | Wallerstein et al. |
| 6,424,377 B1 | 7/2002 | Driscoll, Jr. et al. |
| 6,426,774 B1 | 7/2002 | Driscoll, Jr. et al. |
| 6,449,103 B1 | 9/2002 | Charles |
| 6,597,520 B2 | 7/2003 | Wallerstein et al. |
| 6,885,509 B2 * | 4/2005 | Wallerstein et al. ........ 359/725 |
| 2001/0010555 A1 | 8/2001 | Driscoll, Jr. |
| 2002/0126395 A1 | 9/2002 | Gianchandani et al. |
| 2002/0154417 A1 | 10/2002 | Wallerstein et al. |
| 2002/0159166 A1 | 10/2002 | Herman et al. |
| 2003/0095338 A1 | 5/2003 | Singh et al. |
| 2003/0099045 A1 * | 5/2003 | Doi ........................... 359/725 |
| 2004/0008407 A1 * | 1/2004 | Wallerstein et al. ........ 359/362 |
| 2004/0008423 A1 * | 1/2004 | Driscoll et al. ............. 359/725 |

FOREIGN PATENT DOCUMENTS

| | | |
|---|---|---|
| WO | WO 03/026272 A2 | 3/2003 |
| WO | WO 03/046632 A1 | 6/2003 |

* cited by examiner

OPTICAL LENS PROVIDING OMNI-DIRECTIONAL COVERAGE AND ILLUMINATION

FIELD OF THE INVENTION

The present invention relates to the field of extremely wide-angle imaging. More specifically, it relates to optical structures that enable the coverage and/or illumination of a panoramic or nearly spherical field of view, suitable for video or still imaging.

BACKGROUND OF THE INVENTION

Imaging of a large field of view has many applications in the fields of defense, security, monitoring, entertainment, industry, medical imaging and many other fields. Imaging of a panoramic or nearly spherical field of view, using a single image-capturing device, is especially applicable for a variety of needs due to its relative simplicity, low-cost and miniaturization possibilities.

Security cameras often require the ability to view as large a field of view as possible to enable imaging of all occurrences in a scene for purposes of real-time surveillance and warning or for documentation and restoration of images at later stages.

Inner body imaging during diagnostic or therapeutic medical procedures requires real time viewing of a large field of view in order to provide the surgeon with the ability to orientate and maneuver the medical scope within the body without endangering body organs or risk causing damage to body tissue. These applications also require the ability to illuminate the scene that is imaged in order to provide a clear and understandable image to the physician.

Additional applications, which require a large field of view exist, include remote operation of ground vehicles, imaging equipment for reconnaissance and information gathering, viewing the interior of devices such as engines, and cinematic and home entertainment applications.

One of the prior art techniques of panoramic imaging makes use of several image capturing devices, each one aimed at a different sector limited in width, combined in a manner such that all of them together, when properly aligned, cover a full 360 degrees field of view. Another prior art method for panoramic imaging relies on a single image-capturing device, rotated around a vertical axis. In this method the image-capturing device covers a limited sector at any single moment; but, while completing a full rotation, it creates a sequence of images, which are combined together to form a panoramic image.

The main disadvantage of these prior art methods is their relative complexity. Some prior art methods make use of moving/rotating mechanisms, which require frequent alignment and very often turn out to be maintenance-intensive.

The ability to make use of a single imaging device, equipped with an optical structure, which would enable viewing of the entire perimeter around the imaging device, would be invaluable for the applications described hereinabove.

A prior art approach using a single imaging device makes use of axi-symmetric reflective surfaces to reflect a panoramic field of view towards a single image-capture device. In this approach a circular image is formed on the focal plane array of the image-capturing device. The shape of the image derives from the reflection of the surrounding field of view by the reflective lens, and often includes aberrations. The image shape and additional aberrations are corrected by image processing techniques. Such a prior art design is described in U.S. Pat. No. 6,028,719, in which a method for capturing a nearly spherical field of view using a single axi-symmetric reflective mirror with a hole in its center is described. The main disadvantages of the methods described in U.S. Pat. No. 6,028,719 include the relatively complex fabrication of the optical components to achieve high optical performance, the high fabrication costs of the imaging device and its sensitivity to environmental conditions. Furthermore, such devices provide relatively poor image quality.

A simpler, cheaper and more robust solution for imaging and/or illuminating a panoramic or nearly spherical filed of view would be to use an aspheric optical block, a single image capturing device and in some embodiments—an illumination source. Attempts to fabricate such a device have been made, e.g., in U.S. Pat. No. 6,341,044, which makes use of an optical block and a single image capturing device to provide panoramic imaging. The design used in U.S. Pat. No. 6,341,044 includes a spherical optical block having one refractive surface and one reflective surface. The spherical shape of the optical block and the existence of a single refractive surface incorporated within the optical block itself introduce aberrations that must be corrected by several sets of additional optical lenses along the optical path, as described extensively in the patent.

It is therefore an object of the present invention to provide an optical block designed to provide a reflection of a panoramic perimeter, having an acceptable level of distortions and aberrations.

It is another object of the present invention to provide an optical block designed to enable acquiring of a nearly spherical field of view.

It is another object of the present invention to provide an imaging assembly, based on the optical block of the invention.

It is yet another object of the present invention to provide a method of illuminating the scene that is imaged, simultaneously while imaging; utilizing the same optical block for both coverage of the scene and the transmittance of illumination to the scene.

Further purposes and advantages of this invention will appear as the description proceeds.

SUMMARY OF THE INVENTION

The present invention provides a wide-angle imaging assembly comprising a main lens produced from an aspheric optical block. The aspheric optical block comprises the following elements:
 a. A vertical axis of symmetry;
 b. A transparent upper surface, at least part of which is capable of reflecting rays that impinge upon it from the inner side of said optical block;
 c. A transparent perimeter surface; and
 d. A transparent lower surface.

The material of which the optical block is fabricated is selected to enable optical transmittance of light in a specific spectral range.

Light rays in the specific spectral range that originate in a first scene which has a 360 degrees panoramic perimeter are refracted by the transparent perimeter surface and enter the optical block. They are then reflected by the upper surface towards the transparent lower surface, refracted by the transparent lower surface, and exit the main lens through the transparent lower surface.

The upper surface of the wide angle imaging assembly of the invention can be at least partially, axi-symmetrically coated with reflective material on its exterior side. The reflective coating will cause reflection of light rays that impinge upon the upper surface from the inner side of the optical block. The reflective material that coats the upper surface can be selected to enable reflection of light rays in the specific spectral range transmitted by the material of the optical block.

The wide angle imaging assembly of the invention may further comprise a transparent area in a part of the upper surface around the vertical axis of symmetry. The transparent area enables light from a second scene, located at least partially above the first scene, to pass through the transparent area and travel through and exit the optical block. The curvature of the surface of the transparent area can be different from the curvature of the remainder of the upper surface. The lower surface can be described by two different axi-symmetric curves.

The transparent area can be fabricated in the form of a hole extending along the vertical axis of symmetry. The hole can extend from the upper surface to the lower surface and can have a conical shape. An optical structure designed to enhance or correct light rays coming from the second scene can be placed within the hole. The optical structure placed within the hole can comprise a plurality of optical components.

In another embodiment, the wide angle imaging assembly of the invention further comprises an optical structure located above the transparent area and coaxially with it. The optical structure is designed to enhance or correct light rays coming from the second scene or to enlarge the aperture of the second scene and can comprise a plurality of optical components.

The wide angle imaging assembly of the invention can further comprise a conically shaped hole extending along the vertical axis of symmetry from the upper surface to the lower surface and a black cone designed to prevent glare compatibly shaped to be placed inside the hole.

The wide angle imaging assembly of the invention can further comprise a holding element that is fabricated together with and as part of the optical block. The holding element is located adjacent to the lower surface and extends downwards. The holding element does not interfere with or block the rays that exit from the lower surface. The holding element can have the shape of a tube made of an optically transparent material.

The wide angle imaging assembly of the invention may further comprise a mechanical connector having a first edge and a second edge. The first edge of the connector can be designed to connect to the holding element. The second edge of the connector can be designed to connect to an image capture device, such that the image capture device is positioned coaxially with the optical block, facing the block's lower surface. The mechanical connector may further comprise optical lenses positioned coaxially with the optical block and designed to enhance the quality of the images exiting the lower surface of the optical block. The second edge of the connector can be designed to connect to an illumination source so that it positions the illumination source adjacent to the exterior edge of the holding element.

The wide angle imaging assembly of the invention can further comprise an image capture device designed to capture images that arrive from the optical block. The spectral range, to which the image capture device is sensitive, is at least partially identical to the specific spectral range to which the optical block is transparent.

The wide angle imaging assembly of the invention can further comprise an illumination source that distributes illumination rays, which travel through the holding element and are distributed by the surfaces of the optical block. The wavelength of the illumination source is within the range of the specific spectral range to which the optical block is transparent. The wide angle imaging assembly can comprise a plurality of illumination sources, capable of emitting more than one wavelength. All of the illumination wavelengths are within the specific spectral range to which the optical block is transparent.

In another embodiment the wide angle imaging assembly of the invention can further comprise:
   a. An axi-symmetric lens, capable of reflecting a second panoramic scene, which is at least partially included in the first scene. The axi-symmetric lens is positioned coaxially with and above the optical block.
   b. A hole extending along the vertical axis of symmetry of the optical block.
   c. An optical assembly located within the hole comprising at least a prism or reflective surface. The prism or reflective surface designed to refract or reflect light rays that are reflected by the axis-symmetric lens.
   d. A compatibly positioned image capture device The axi-symmetric lens is capable of transmiting light rays in a second spectral range which is at least partially different than the specific spectral range to which the optical block is transparent. The optical assembly does not interfere or block the rays reflected from the optical block. The first panoramic scene provided by the optical block in the specific spectral range is at least partly identical to the panoramic scene provided by the axi-symmetric lens in the second spectral range.

All the above and other characteristics and advantages of the invention will be further understood through the following illustrative and non-limitative description of preferred embodiments thereof, with reference to the appended drawings. It is stressed that the particulars shown are by way of example and for purposes of illustrative discussion of preferred embodiments of the present invention only. No attempt is made to show in the drawings structural details of the invention in greater detail than is necessary for understanding of the invention. Skilled persons will readily understood details not shown in the figures will easily appreciate how the several embodiments of the invention may be carried out.

DETAILED DESCRIPTION OF PREFERRED EMBODIMENTS

Figure 1:
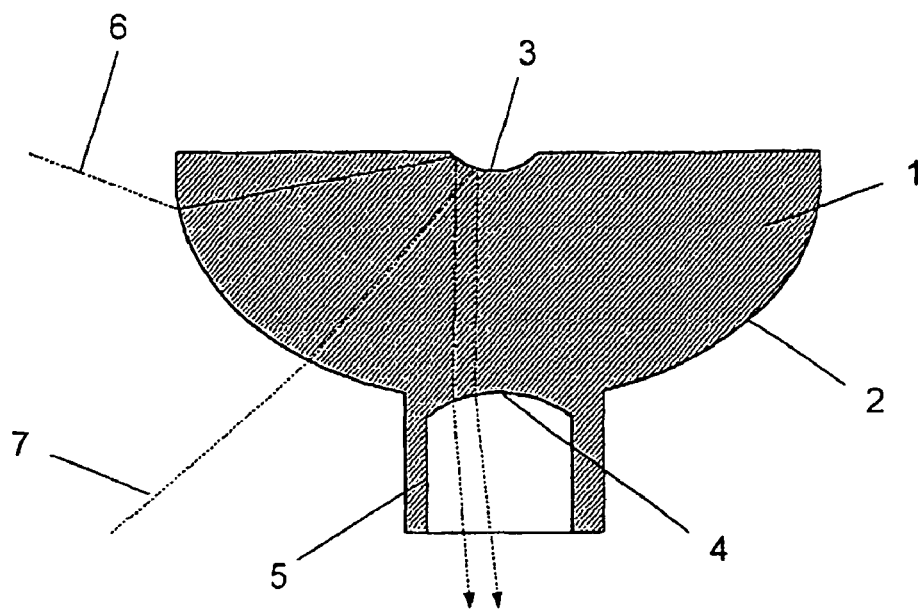
FIG. 1 shows schematically an embodiment of an aspheric optical block that provides coverage of a panoramic scene.

The preferred embodiments of the present invention are described hereinbelow with reference to the figures. All of the figures show a cross-sectional view of only the main optical components of an electro-optical system. The system is designed to produce an image of a cylindrical or nearly spherical field of view. The main optical components, which are shown, are generally those that are responsible for gathering the light rays from the cylindrical or nearly spherical field of view at the same instant, and directing those light rays to the other components of the system. As it is clear that several different components comprise the entire electro-optical system, reference to only the main optical components is made for the sake of brevity and since other components and their incorporation in the system are known from the prior art and are well within knowledge of those skilled in the art. The figures are schematic and designed to provide a general perception of preferred embodiments of the present invention. In some of the figures are shown optical paths of light rays that travel through the optical system. These paths are schematic and they are shown in order to make apparent the course of refraction and/or reflection of the rays by the main optical components of the system. In all of the figures there is shown a solid axi-symmetric optical lens, which is responsible for the actual direction of the surrounding scene towards an image capture device or towards other optical components. The solid axi-symmetric optical lens is referred to as the "main lens". Several different embodiments are described in order to demonstrate the variety of designs and different types of information that can be obtained by use of the different embodiments of the invention. The main lens is produced by known optical fabrication methods such as diamond turning, molding etc. and the material of which the block is produced is selected to enable optical transmittance of a specific spectral range. All of the embodiments of the imaging assembly of the invention comprise a main lens made from an aspheric optical block comprising the following:
  a. A vertical axis of symmetry;
  b. A transparent upper surface, at least part of which is capable of reflecting rays that hit it from the inner side of the optical block.
  c. A transparent perimeter surface; and
  d. A transparent lower surface.

In all embodiments, light rays of the specific spectral range originating in a first scene having a 360 degrees panoramic perimeter are refracted by the transparent perimeter surface, enter the aspheric block, are then reflected by the upper surface towards the transparent lower surface, are then refracted by the transparent lower surface, and exit the main lens through the transparent lower surface.

It is stressed that besides the main lens, additional components are required to make best benefit of the present invention. Those additional components, may include, but are not limited to:
  a. An image capture device, located, directed, and set in a manner that enables the capture of an optimal image that is produced by the main lens. In preferred embodiments of the present invention, the image capture device is located coaxially with the main lens. The image capture device is preferably equipped with a focusing lens, set to capture a focused image depending on the distance of the image capture device from the main lens.
  b. Prisms, which are capable of directing the image that is produced by the main lens towards an image capture device, which (in some embodiments) is not located coaxially with the main lens.
  c. Correcting lenses, which may be used to enhance the quality of the image before it is captured by the image capture device. Those correcting lenses are generally positioned between the main lens and the image capture device, and they are selected, designed and positioned as a function of the design of the main lens. The necessity of using correcting lenses may be reduced to a minimum by proper optical design of the main lens in order to reduce astigmatism, aberrations and other optical distortions of light rays to a minimum.
  d. A processing unit that receives, processes, and displays the image that is captured by the image capture device.

In FIG. 1 is schematically shown a preferred embodiment of the present invention. In this figure there is shown a design of a main lens (1) that provides a reflection of the perimeter around it and enables the capture of the entire perimeter at the same instant by a suitable image capture device (not shown). The main lens (1) comprises a transparent perimeter surface (2), a transparent upper surface (3), a transparent lower surface (4) and a holding element (5). All of the mentioned surfaces are fabricated as part of a unified mold, or single solid optical component. In a preferred embodiment of the present invention, the upper transparent surface (3) is coated with reflective material on its exterior surface, enabling reflection of light rays that arrive from the direction of the inner side of the main lens (1).

Reference is now made to schematic optical paths of light rays that travel through the main lens (1). A first light ray (6), originating in the field of view that is covered by the main lens (1), penetrates the main lens's transparent perimeter surface (2), where it is refracted. The ray (6) then travels through the solid medium of the main lens (1) and is incident upon the inner side of the upper surface (3). As a result of the reflective coating on the exterior of the upper surface (3), the ray (6) is then reflected towards the lower transparent surface (4), where it is refracted again and exits the main lens (1). Light ray (7) travels a similar optical path, being refracted and reflected by the same surfaces as ray (6).

According to another preferred embodiment of the present invention, the upper surface (3) may remain entirely or partly uncoated. In this case, the light rays, which hit the upper surface (3) from the inner side of the main lens (1), are reflected according to Snell's Law of Total Internal Reflection. Those skilled in the art will appreciate that by not using a reflective coating, and leaving a part (or all) of the upper surface (3) uncoated, a different field of view may be covered by the main lens (1). Therefore the choice of whether or not to use a reflective coating depends on the requirements of the specific application, and the design of the main lens.

It is further stressed that the exact shape of the main lens's surfaces is not random, and each surface is designed according to the desired field of view to be covered, the required angular resolution, and additional parameters which are known to those skilled in the art. Each surface's design is affected by the design of the other surfaces, therefore the design is done by constantly considering the mutual affect that each surface has on the field of view which is covered, chromatic or other aberrations and/or distortions that might be caused to light rays along their path etc.

It is preferable to fabricate the main lens together with a holding element (5), which is also a part of the unified mold, in a shape that enables direct connection of the main lens (1) to an image capture device, or other mechanical component or connector.

Figure 2:
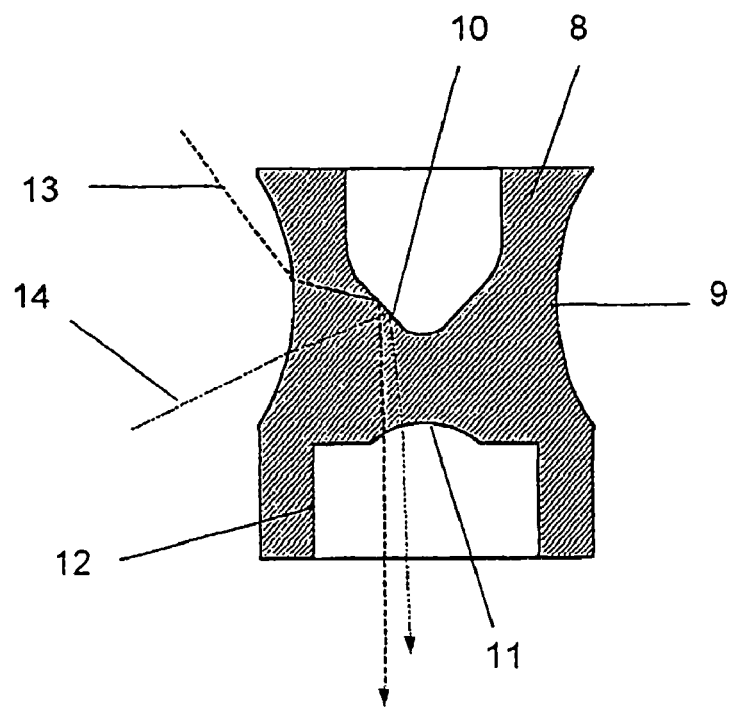
FIG. 2 shows schematically another embodiment of an aspheric optical block that provides coverage of a panoramic scene.

In FIG. 2 is schematically shown a second preferred embodiment of the main lens (8). This embodiment also includes a transparent perimeter surface (9), a transparent upper surface (10), a lower surface (11) and a holding element (12). Perimeter surface (9) is a negative optical surface that enables the capture of a larger vertical field of view than that captured by the embodiment of the main lens shown in FIG. 1. Two light rays, (13) and (14) represent schematic optical paths of light rays that travel through the main lens (8). In this embodiment as well as in that shown in FIG. 1, it is possible to exploit Snell's Law of Total Internal Reflection and not to coat all or part of the upper surface with reflective coating.

Figure 3:
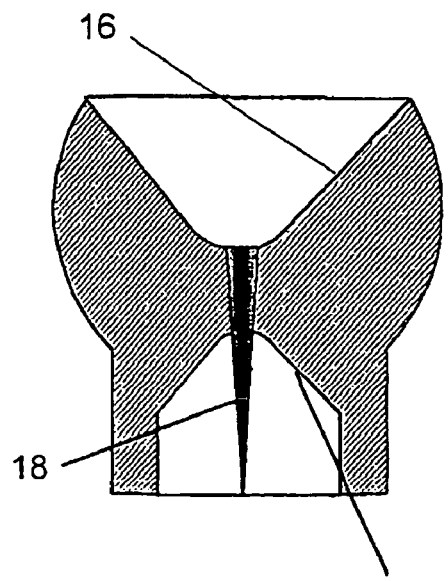
FIG. 3 shows schematically another embodiment of an aspheric optical block that provides coverage of a panoramic scene, equipped with a component for glare reduction.

In FIG. 3 is schematically shown an embodiment of the imaging assembly of the invention that incorporates within the main lens an additional component that reduces glare. In this embodiment, the main lens (15) comprises a hole in its center, extending along its central axis, from its upper surface (16) to its lower surface (17). The hole is preferably conically shaped. Inside the hole there is placed a blackened cone (18) that preferably extends through the entire thickness of the main lens (15) and extends downwards below the lower surface (17). The cone (18) is designed to absorb light rays that may be reflected or dispersed to undesired directions and cause glare that is visible in the final image. The undesired glare is a side-affect, which appears in varying intensities as a function of the optical design of the main lens. Therefore the incorporation of the blackened cone is optional and dependent on the intensity of the glare.

Figure 4:
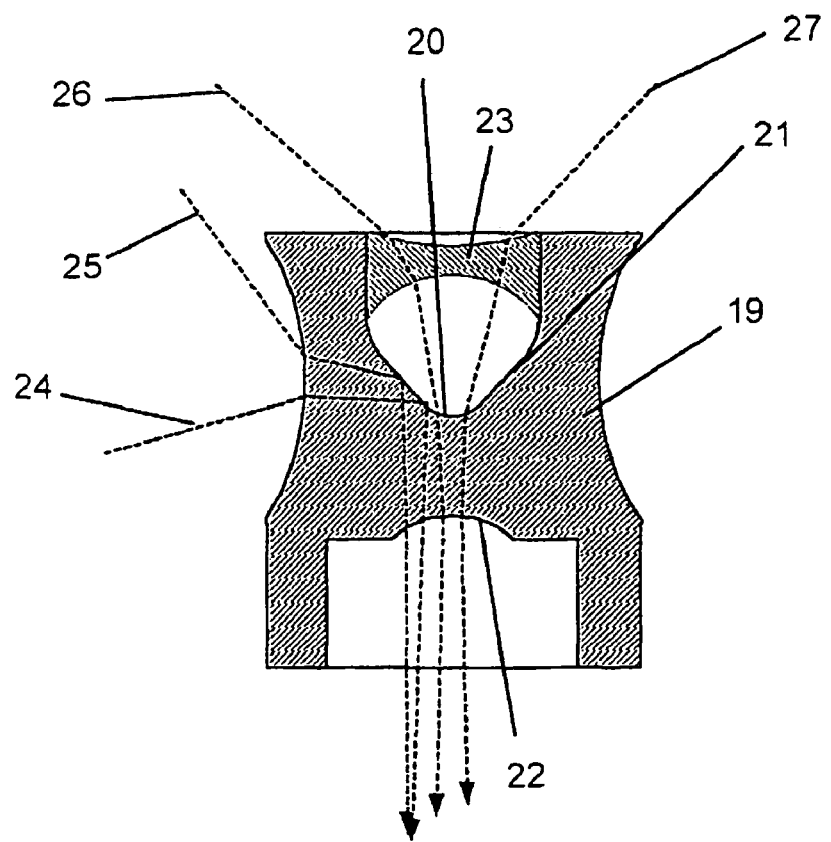
FIG. 4 shows schematically an embodiment of an aspheric optical block that provides coverage of a nearly spherical scene.

In FIG. 4 is schematically shown an embodiment of a main lens that is capable of covering a nearly spherical field of view. In this figure the main lens (19) comprises a transparent area (20) located at the center of the upper surface (21). The transparent area (20) is axi-symmetric and may be fabricated either as a hole, extending from the upper surface (21) downwards to the lower surface (22), or simply as an area of upper surface (21) which is not coated with reflective material. If a hole is not implemented, it is possible to fabricate the transparent area (20) as an area having a different curvature than that of the upper surface (21). In this way a lens effect may be achieved simply by proper design of the transparent area's curvature. The presence of transparent area (20) enables coverage of a field of view above the upper surface (21), which is additional to the cylindrical field of view that is generally captured by the embodiments described hereinabove. It is possible to combine additional optical elements (23) coaxially and above the transparent area (20) that would enable control over the size and optical qualities of the additional scene that is covered. The form of the main lens (19) shown in FIG. 4 enables relatively convenient positioning of the additional optical components (23) within the niche that exists above the upper surface (21). However, it is stressed that the principles of the method of covering the additional scene, as shown in this figure, are applicable mutatis mutandis to other embodiments of the main lens. Each embodiment of the main lens might impose a different design of the optical components (23) and may require mechanical adaptors or special connection methods of the additional optical components (23) to the main lens (19). Those connection methods are well known to those skilled in the art, and have been presented in prior art, therefore no further reference is made to connection of optical components amongst themselves.

Reference is now made to optical paths of light rays that travel through the main lens (19). Light rays (24, 25), which originate in the cylindrical field of view covered by the main lens (19), travel the same path as light rays (13, 14) shown in reference to FIG. 1. Light ray (26), which originates in the additional scene, not included in the cylindrical scene, is refracted by the additional optical component (23), if such component is present. The ray (26) then travels towards the transparent area (20) where it is refracted again and travels through the main lens (19) until reaching its lower surface (22) where it exits the main lens (19). An additional light ray (27) travels essentially the same course as ray (26). Light ray (26) and light ray (27) represent the edges of the additional scene that is covered (i.e. the aperture of the scene). As previously described, the aperture may be controlled by the selection and/or design of the optical components (23) and/or of the curve of the part of the surface defining the transparent area (20).

Figure 5:
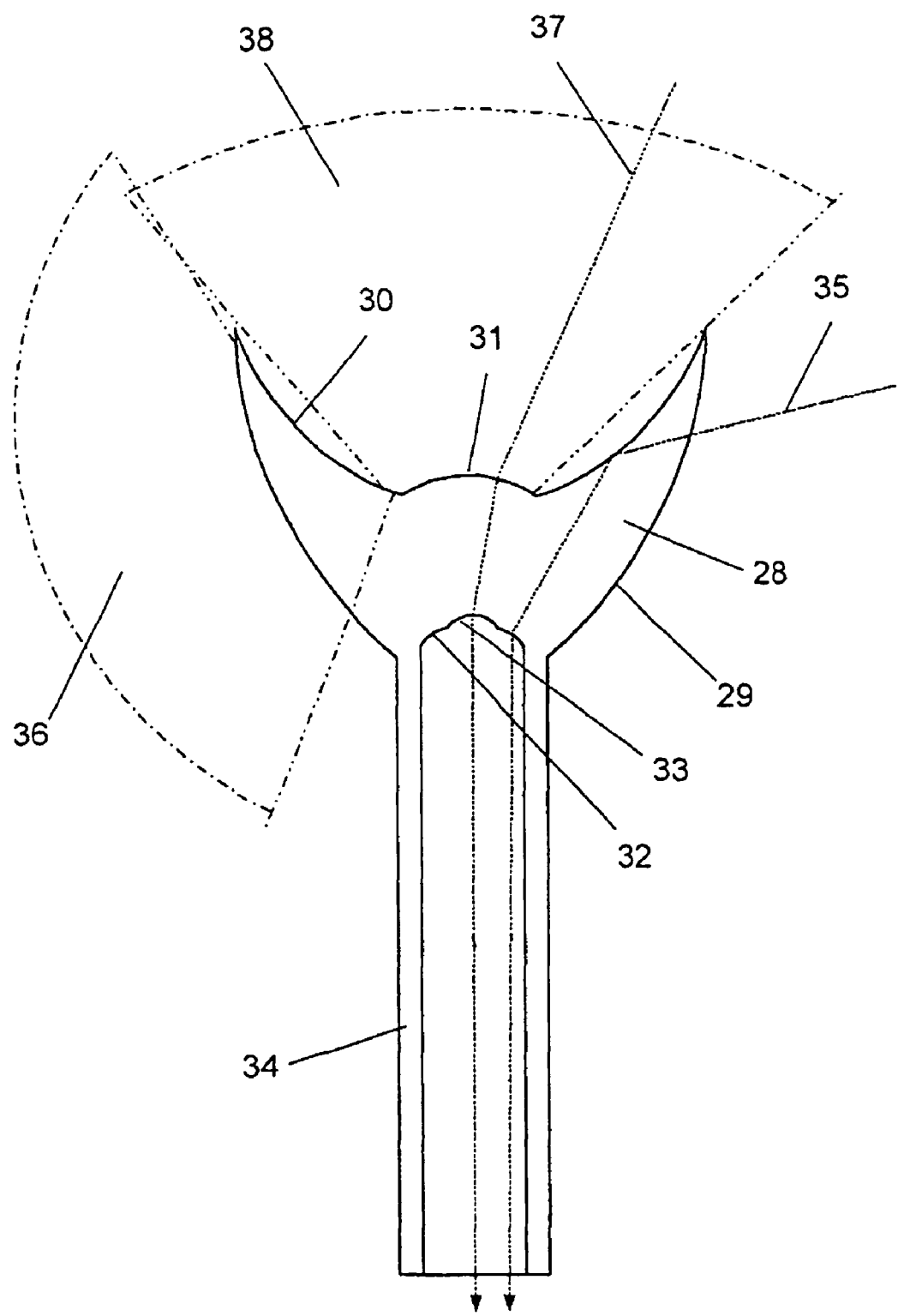
FIG. 5 shows schematically an optical structure that enables coverage of a nearly spherical field of view.

In FIG. 5 is schematically shown another embodiment of main lens that enables coverage of a nearly spherical field of view. In this embodiment the main lens (28) comprises a transparent perimeter surface (29), a transparent upper surface (30), a central transparent upper surface (31), a lower transparent surface (32) and a central transparent lower surface (33). Additionally, the main lens (28) comprises a holding element (34). A first light ray (35) represents a light ray that originated within the range of the cylindrical scene (36) that surrounds the main lens (28) and that is covered by the main lens (28). The light ray (35) is refracted by the perimeter surface (29), travels through the solid medium of the main lens (28), hits the upper surface (30), is reflected downwards towards the lower surface (32) where it is refracted again, and exits the main lens (28). A second light ray (37) represents a light ray that originates above the central upper surface (31) in a scene (38) that is covered by the central upper surface (31). The second light ray (37) is refracted by the central upper surface (31), penetrates the main lens (28), travels through the lens's solid medium, is refracted by the central lower surface (33), and exits the lens. All light rays originating in the cylindrical scene (36) and in the additional scene (38) together comprise a nearly spherical scene.

In FIG. 5, the central upper surface (31) and the upper surface (30) are shown as having two different curvatures, however, they may be fabricated as a single curved surface, depending on the application, the desired field of view etc. In the same way, the central lower surface (33) and the remainder of the lower surface (32) which are shown as having two different curvatures, can be fabricated as a single curved surface.

Figure 6:
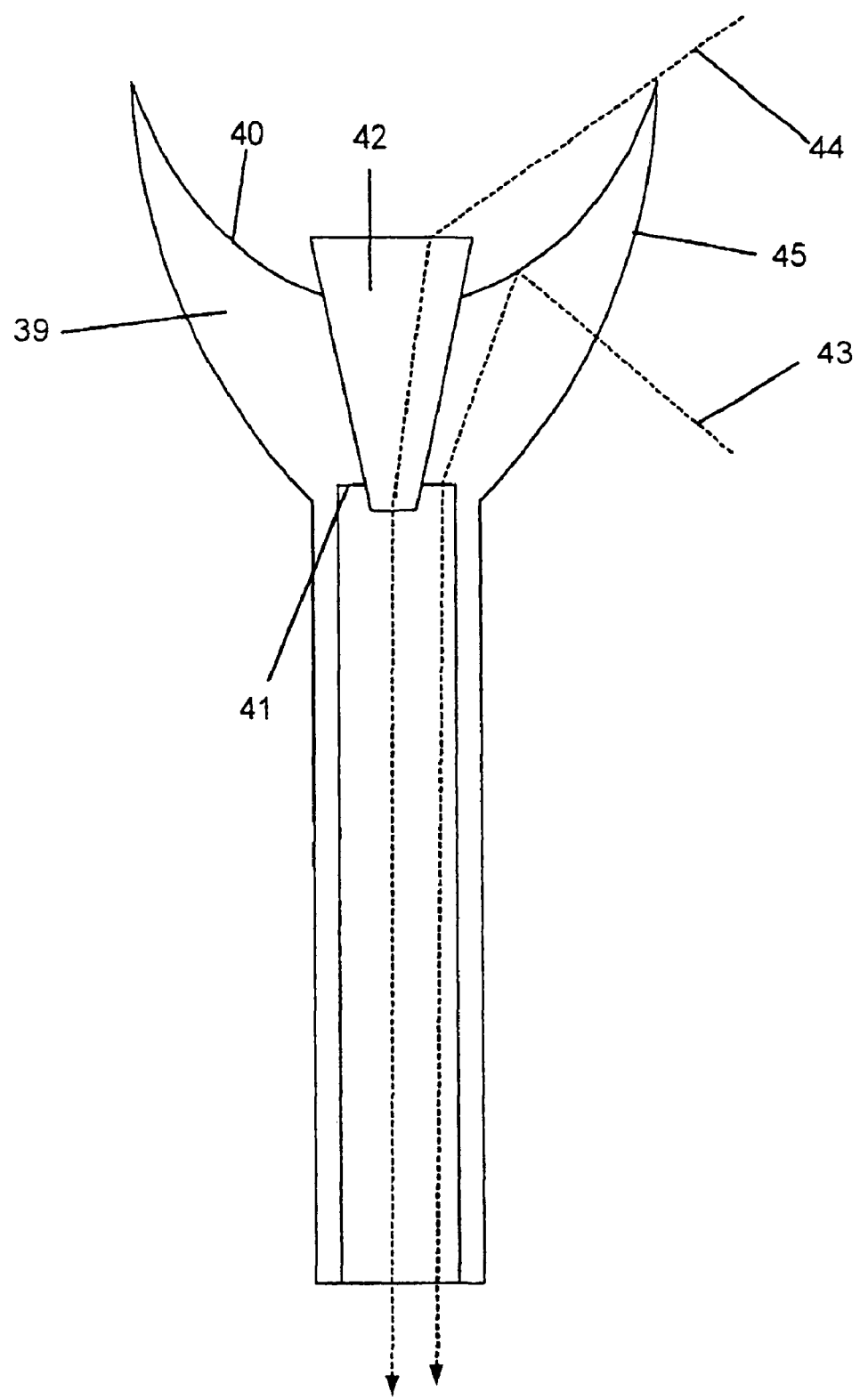
FIG. 6 shows schematically another optical structure that enables coverage of a nearly spherical field of view.

In FIG. 6 is schematically shown yet another embodiment of a main lens that enables coverage of a nearly spherical field of view. In this embodiment, the main lens (39) comprises a hole in its center extending along its central axis of symmetry from the main lens's upper surface (40) to its lower surface (41). The hole is preferably conically shaped. Inside the hole there is placed an optical assembly (42), which may comprise one or more optical components packaged together. The optical assembly is shaped (or packaged in a shape) compatible with the shape of the hole, so that it can be inserted and fastened inside the hole. The optical assembly (42) is designed to refract rays that originate at a scene that is additional to the cylindrical scene surrounding the axis of symmetry of the main lens (39). A first light ray (43) represents a ray that originates in the cylindrical scene and a second light ray (44) represents a ray that originates in an additional scene located above the upper surface (40) of the main lens (39). Light ray (43), originating in the cylindrical scene, is refracted by the perimeter surface (45), then reflected by the upper surface (40) towards the lower surface (41), then refracted by the lower surface (41), and exits the main lens (39). Light ray (44), which originates in the additional scene, is refracted by the optical assembly (42). The optical assembly (42) may include one or more optical components; therefore, the ray (44) may be refracted more than once, depending on the number of optical components comprising the optical assembly (42). The rays originating in the additional scene exit the optical assembly (42) and can be captured by the same image capture device that is designed to capture the rays that originate in the cylindrical scene. Therefore the same image capture device may capture a nearly spherical scene.

Figure 7:
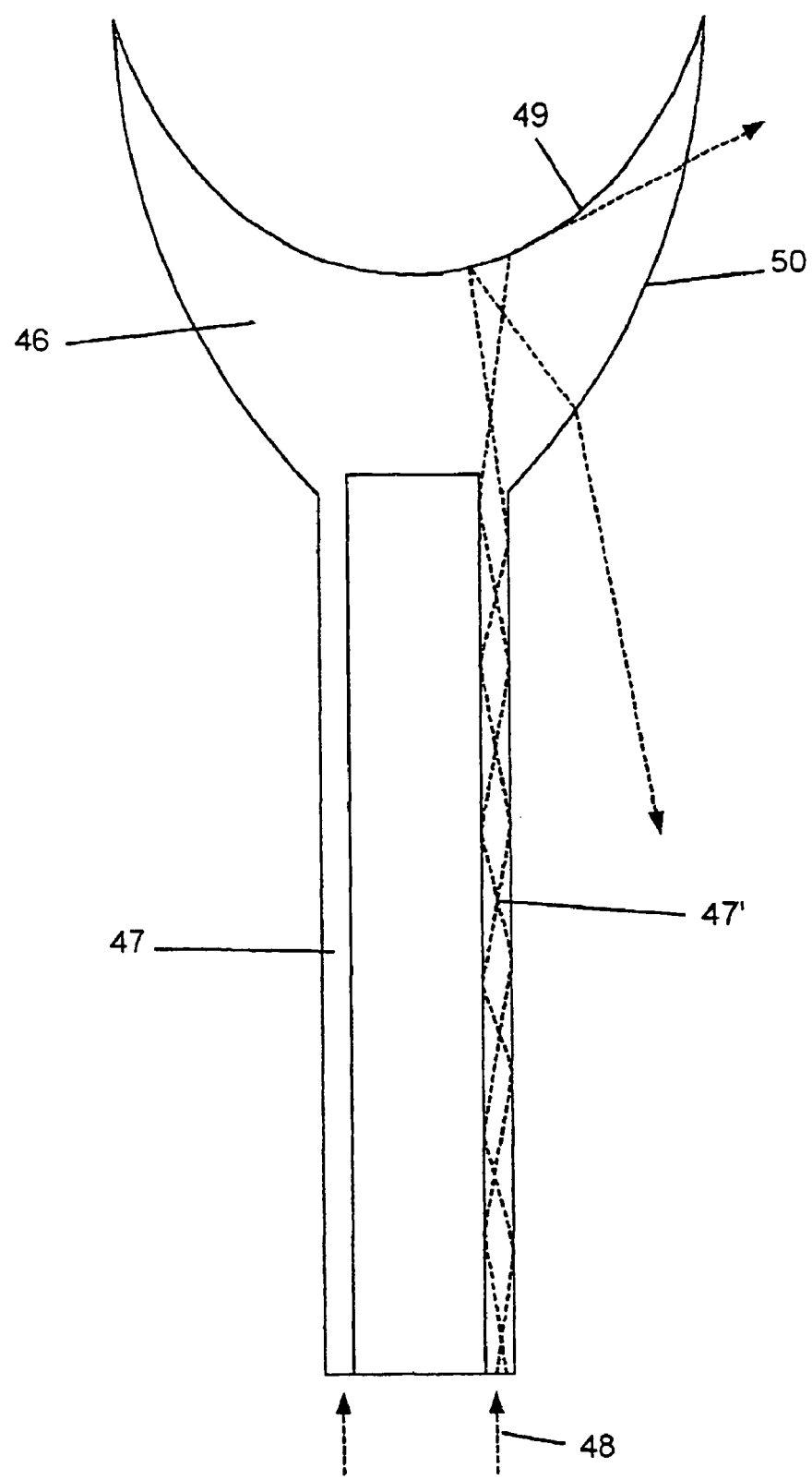
FIG. 7 shows schematically an optical structure also used for distribution of illumination to a panoramic scene.

In FIG. 7 is schematically shown an embodiment of the imaging assembly of the invention that utilizes the form of the main lens (46), which is used for capturing the omni-directional scene, to simultaneously distribute illumination to the scene that is to be imaged, therefore enabling image capture in limited lighting conditions. The main lens (46) is preferably fabricated with a holding element (47). All or part of the structure of the holding element can be utilized as an illumination conductor (47'). Illumination sources (48) may be located at the end of the illumination conductor (47'). The light originating at the illumination sources (48) penetrates the illumination conductor (47') and travels along the illumination conductor (47') until reaching the main lens (46). The illumination rays travel through the solid medium of the main lens (46), hitting its upper surface (49) and reflected by it towards the perimeter surface (50). The illumination rays are then refracted and exit the main lens (46) thus illuminating the scene located around the main lens (46). It is stressed that the length of the holding element (47) may be determined to achieve optimal light conduction. The holding element (47) should be fabricated from a material that is transparent to the wavelength/s of light emitted by the source, thus enabling optimal light conduction from one end of the illumination conductor (47') to the main lens (46). The illumination conductor may be fabricated as a tube, which is separate from the main lens (46), meaning that a separate illumination conductor is connected to the holding element. The area of connection between the separate illumination conductor and the holding element should enable penetration of light rays from the illumination conductor into the part of the streucture of the holding element that functions as the illumination conductor and from there to the main lens (46). It is stressed that the incorporation of illumination sources in the system does not compromise its image capture capability. It is further stressed that the illumination source may be chosen to be in one or more different wavelengths (not necessarily the visible spectrum). However it is important to choose the fabrication material according to the spectrum of the illumination source, to ensure that the illumination conductor (47') and the main lens (46) are transparent to the illumination wavelengths.

Figure 8:
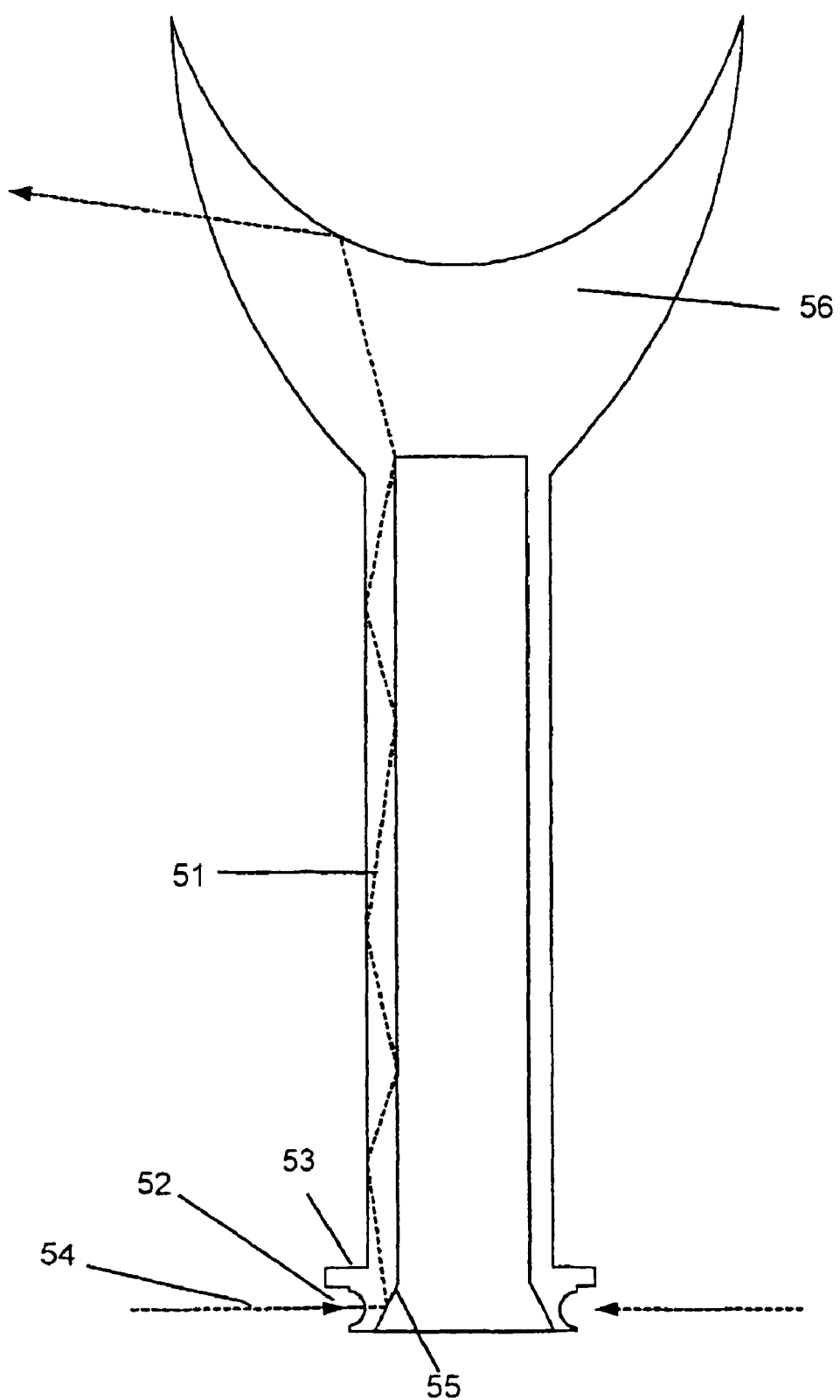
FIG. 8 shows schematically an illumination conductor used to conduct the illumination from an illumination source to the optical block.

In FIG. 8 is schematically shown an embodiment of the imaging assembly of the invention comprising means for interfacing an illumination source with the illumination conductor. According to this embodiment, the illumination conductor (51) includes, or is connected to, an opto-mechanical structure (52) at its end. The opto-mechanical structure (52) comprises connention means (53) designed to be connected to the illumination source and a reflective surface (55) designed to reflect the illumination toward the illumination conductor (51). A light ray (54) originating at an illumination source enters the opto-mechanical structure (52), where it is refracted by the reflective surface (55) to the direction of the illumination conductor (51). From the reflective surface (55) the ray (54) travels through the illumination conductor (51) towards the main lens (56) by which it is reflected and refracted to illuminate the scene surrounding the main lens (56).

Figure 9:
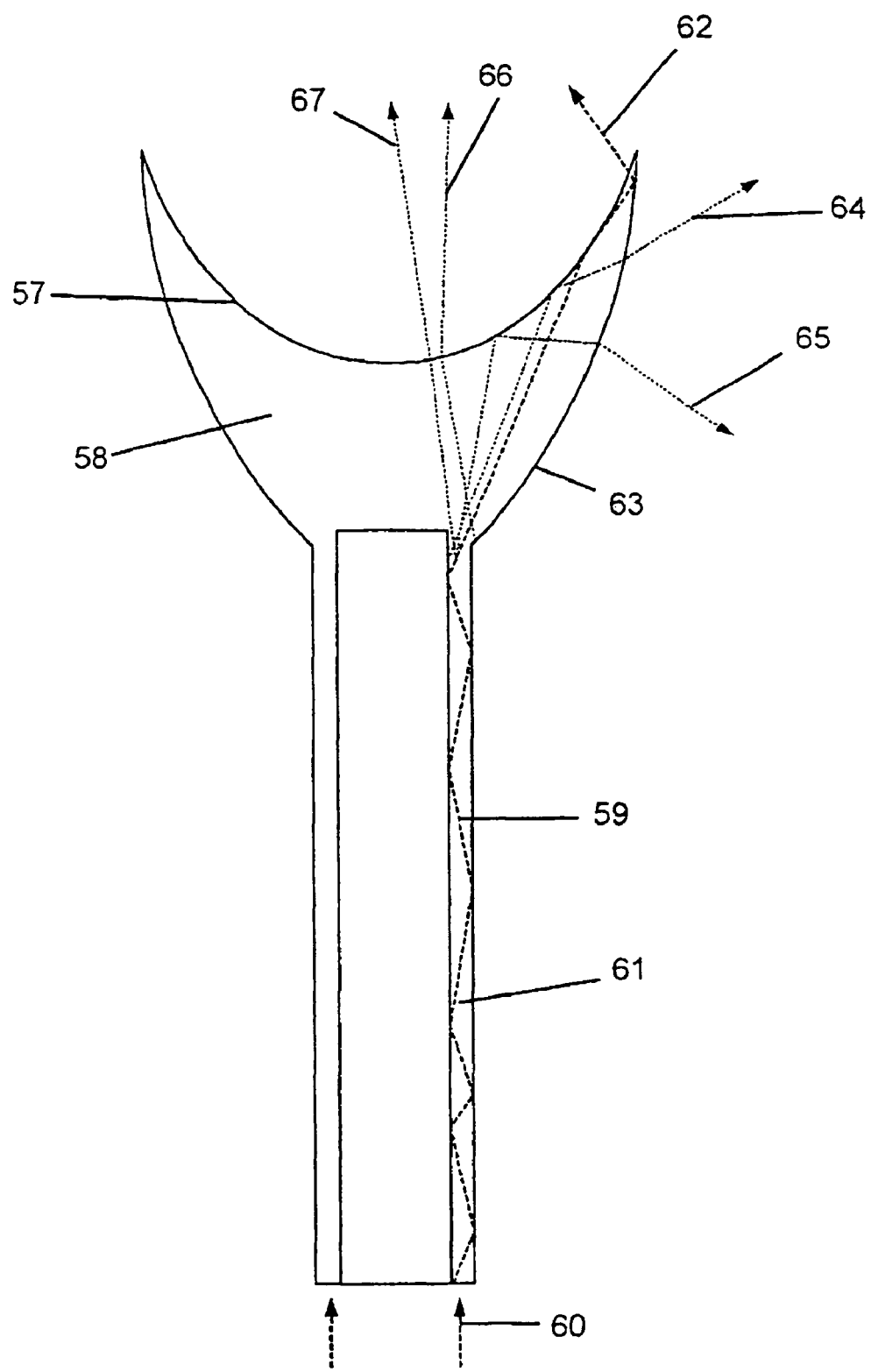
FIG. 9 shows schematically an optical structure also used for distribution of illumination to a nearly spherical scene.

In FIG. 9 is schematically shown an embodiment of a main lens that can be used with a light source to illuminate a nearly spherical scene. According to this embodiment, the upper surface (57) of the main lens (58) is not covered with a reflective coating at all; or, alternately, only a part of the upper surface (57) is coated with a reflective coating. Light rays (59) originating at a light source (60) travel through the illumination conductor (61) until reaching the main lens (58). At the top of the illumination conductor (61) the light rays are dispersed and are incident upon the inner side of the upper surface (57) of the main lens (58) from many different angles. The light rays that are created after hitting the upper surface (57) can be divided into three groups. The first group of rays, represented by light ray (62) is reflected by the upper surface (57) towards the perimeter surface (63). The reflection is either from a reflective coating which coats the upper surface or by total internal reflection, if this is made possible by the specific design of the main lens (58). The ray (62) then hits the perimeter surface (63) where it is reflected again towards a different area of the upper surface (57). The reflection by the perimeter surface results from either reflection from a reflective coating applied to a narrow strip of the perimeter surface or by total internal reflection, if possible. The ray (62) then hits the upper surface (57) and is refracted by it, exiting the main lens (58) and illuminating a part of the scene located above the upper surface (57). It is easily understood that, in order to enable the exit of the first group of light rays from the upper surface (57), the specific area in the upper surface from which the first group of rays is designed to exit, must remain transparent (uncoated).

A second group of light rays, represented by ray (64) and ray (65), is reflected by the upper surface (57) towards the perimeter surface (63). The rays (64, 65) are refracted by the perimeter surface (63) and exit the main lens (58), illuminating a scene located around the axis of symmetry of the main lens (58).

A third group of light rays, represented by ray (66) and ray (67), is refracted by the upper surface (57) and exits the main lens (58) illuminating the part of the scene which is located above the upper surface (57). In order to enable the third group of rays to exit the upper surface (57), the area of the upper surface, from which the rays are designed to exit, must remain transparent (uncoated).

It is stressed that the division into the three groups of light rays described hereinabove may not be applicable to all forms of the main lens. The exact paths the light rays will take is dependant on the angle of total internal reflection and additional parameters such as which area/s is/are coated with reflective coating, the exact shape of and relation between the surfaces of the lens, etc. The purpose of FIG. 9 is to schematically describe the three possible principle groups of light rays that pass through the main lens.

Figure 10:
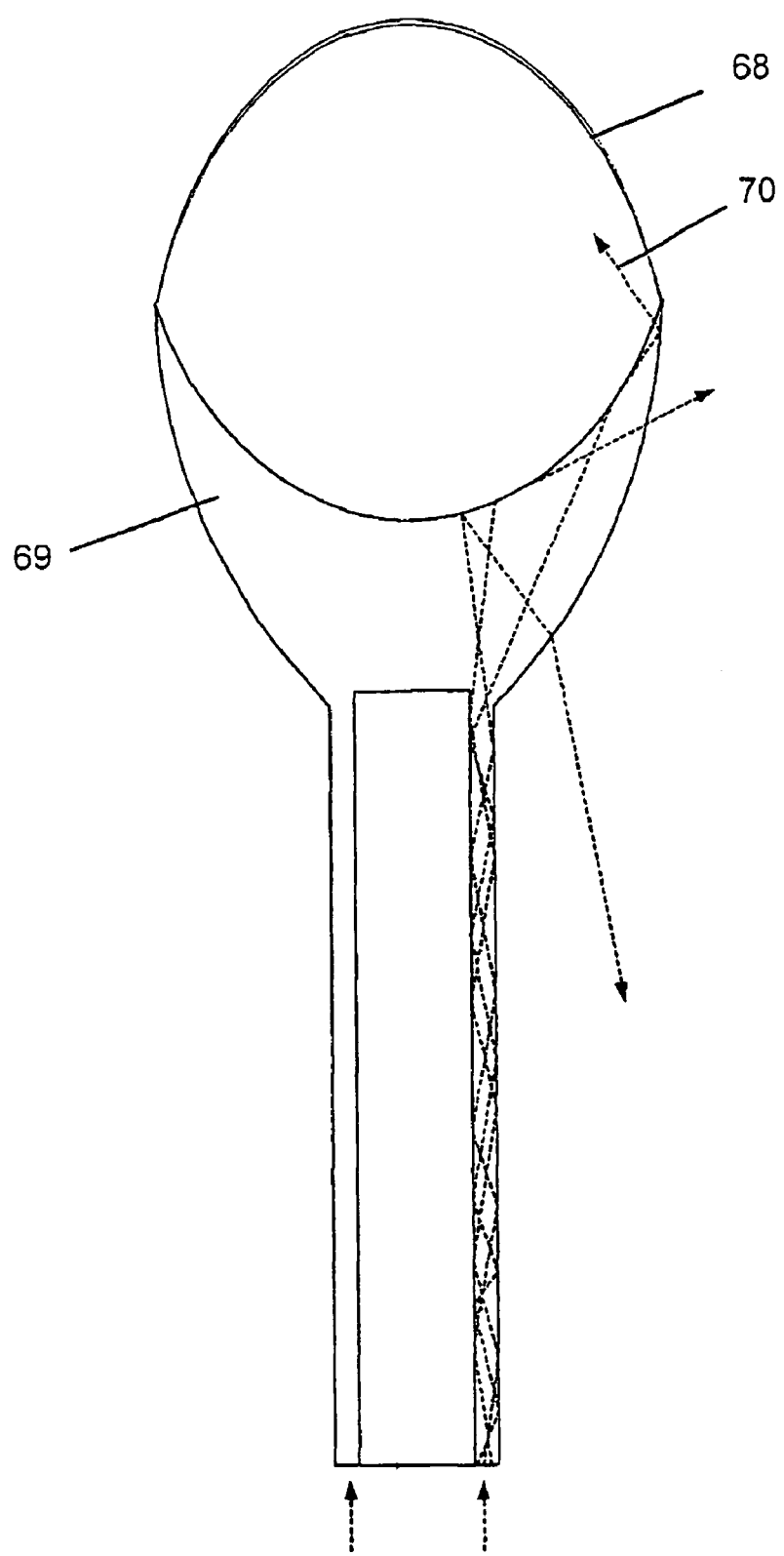
FIG. 10 shows schematically an optical block, equipped with an additional optical component and also used for distribution of illumination to a nearly spherical scene.

In FIG. 10 is schematically shown another embodiment of the main lens comprising a transparent optical dome (68) that is connected to the main lens (69). The dome (68) may serve several possible functions. A first function served by the dome (68) can be to evenly disperse light rays (70) that are provided to illuminate the scene above the dome (68). Light rays (70) exiting the main lens (69) will hit the dome (68) and be dispersed by it to evenly illuminate the scene which is located above the dome (68), thus enabling a clear and glare-free view of the scene. A second possible function of the dome (68) is to complete the structure of the main lens (69) to form an ergonomic structure that will enable smooth and easy insertion of the main lens to body cavities, when the main lens (69) is incorporated in a medical device, designed to image inner body canals, or into other cavities in non-medical applications. A third possible function of the dome (68) is to push away any liquids or solid objects (e.g. body tissue in medical applications) that may stick to the main lens (69) and/or obscure its field of view.

Figure 11:
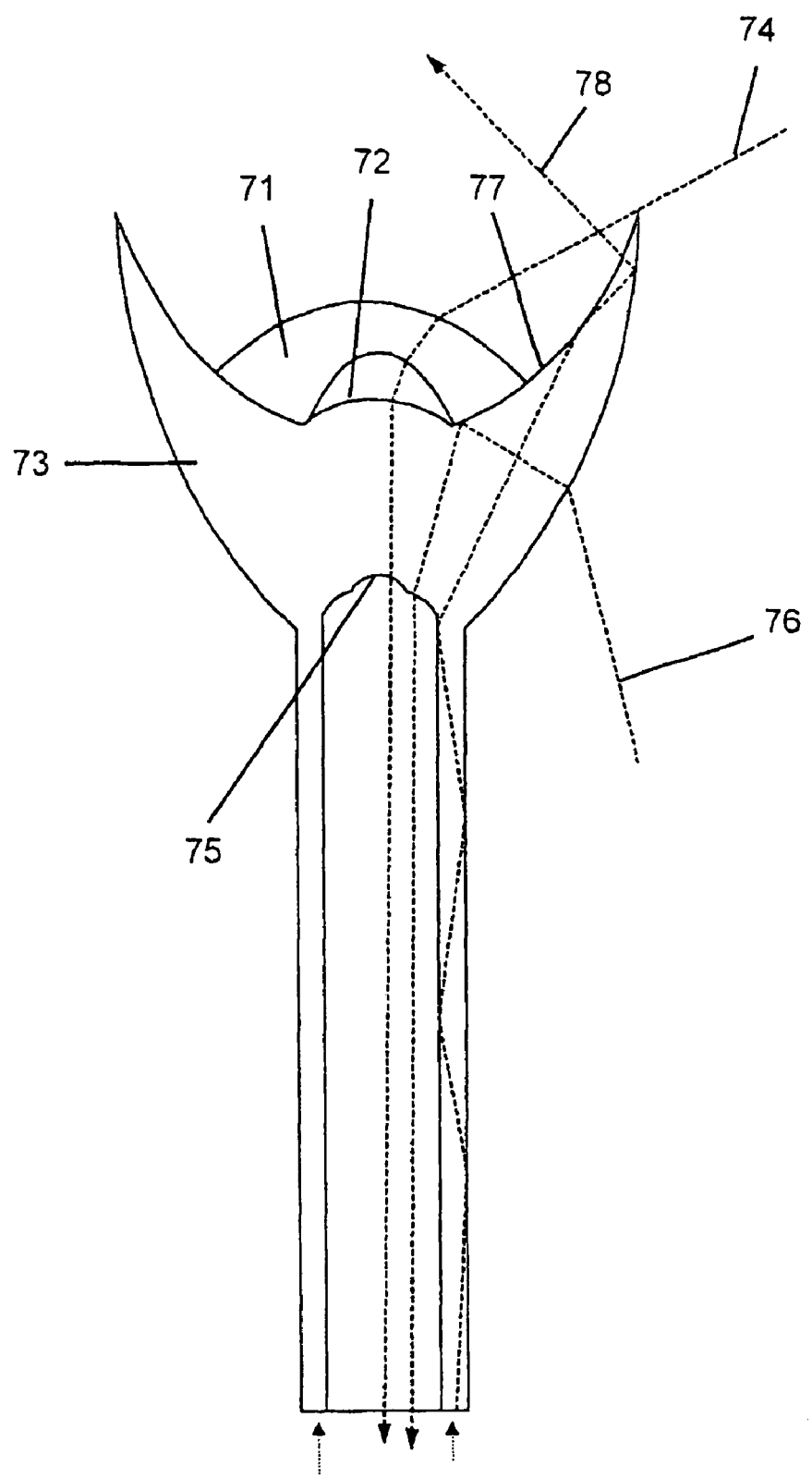
FIG. 11 shows schematically another optical block equipped with an additional optical component and also used for distribution of illumination to a nearly spherical scene.

In FIG. 11 is schematically shown another embodiment of the main lens that provides illumination and imaging of a nearly spherical field of view. In this embodiment, an optical structure (71) is incorporated above the central upper surface (72) of the main lens (73). The optical structure (71) is designed to enlarge the aperture of the scene located above the central upper surface (72) which is covered by the main lens (73) and which is not part of the cylindrical scene surrounding its axis of symmetry. A light ray (74), representing light rays that originate in the field of view covered by the optical structure (71), is refracted by the optical structure (71) towards the central upper surface (72), then refracted again and travels through the main lens (73) until exiting the main lens from its central lower surface (75). An embodiment of the main lens (73), which does not include the optical structure (71), was described with reference to FIG. 5 hereinabove. Comparing the embodiment shown in FIG. 5 with that shown in FIG. 11, it can be seen that the absence of the additional optical structure (71) causes the field of view covered by the central upper surface to be narrower than the one covered with its presence.

In FIG. 11, ray (76) represents rays originating in the cylindrical scene surrounding the axis of symmetry of the main lens (73). The ray (76) takes a similar path to that shown in previous figures for rays originating in the cylindrical scene. It is stressed that the incorporation of the optical structure (71) does not interfere with the path of light ray (76) or with its reflection by the upper surface (77).

Ray (78) represents a light ray designed to illuminate a scene located above the central upper surface (72). It is stressed that the incorporation of the optical structure (71) does not interfere with the path of light ray (78), nor does it block light ray (78) from the scene that it is intended to illuminate.

Figure 12:
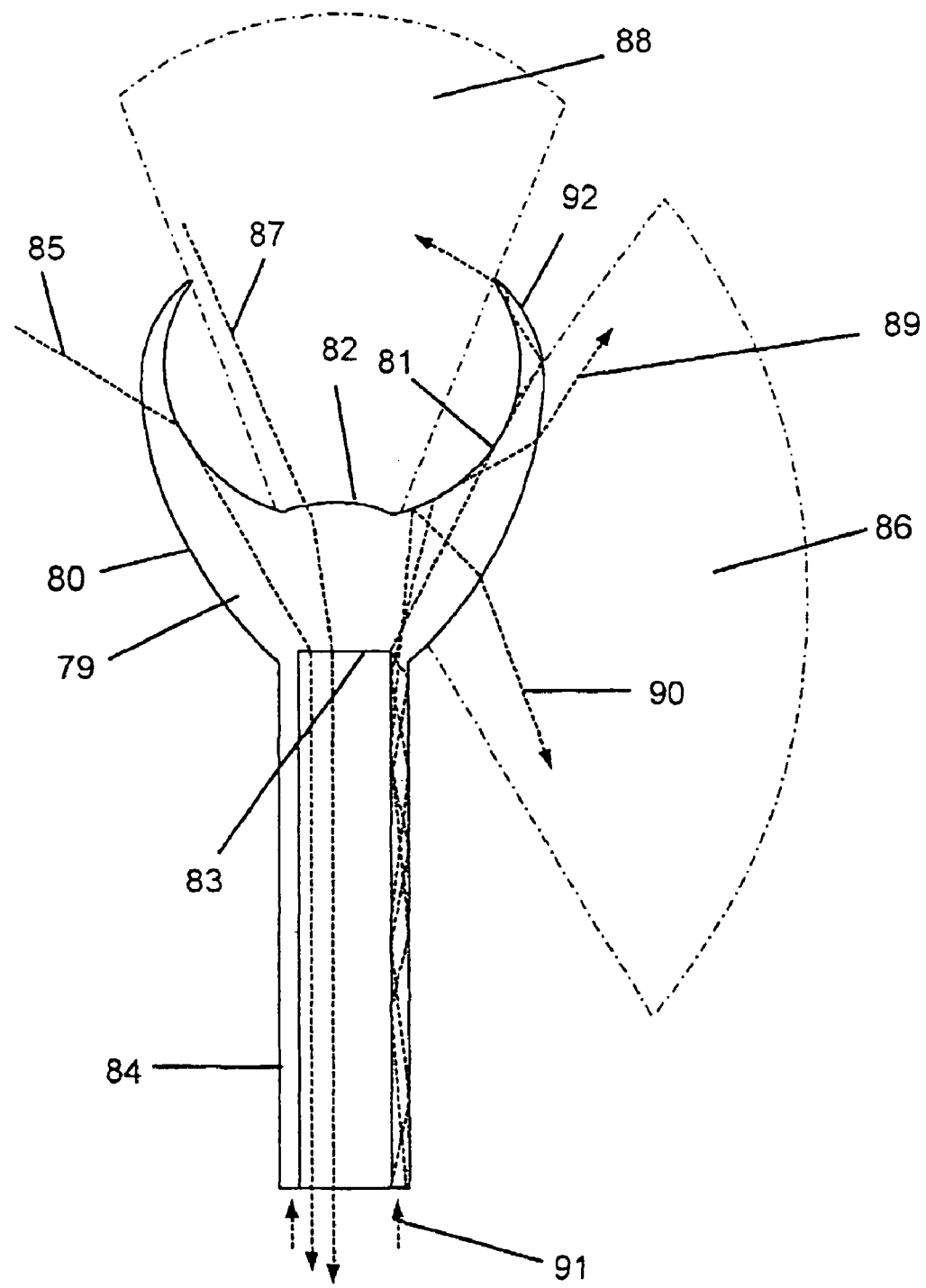
FIG. 12 shows schematically yet another possible design of an optical block that enables both coverage and illumination of a nearly spherical scene.

In FIG. 12 is schematically shown an embodiment of the main lens that provides both coverage and illumination of a nearly spherical field of view. The form of the main lens in this embodiment is ergonomically shaped to enable easy and smooth insertion into, for example, body canals when the main lens is incorporated into a medical device. In the embodiment shown in FIG. 12, the main lens (79) has a perimeter surface (80) that extends upwards as compared to that of the embodiments described hereinabove. The perimeter surface is preferably extended in a circular manner to create the unique ergonomic shape without compromising the optical qualities of the lens. The main lens (79) comprises a transparent perimeter surface (80), a transparent upper surface (81) preferably coated with reflective material on its exterior side, a transparent central upper surface (82), and a transparent lower surface (83), which may be comprised of one or more axi-symmetric curves. Additionally, the main lens comprises a holding element (84), whose length can be determined according to its purpose. The holding element can be used also as an illumination conductor.

A light ray (85) originating in the cylindrical scene (86) that surround the axis of symmetry of the main lens (79) is refracted by the transparent perimeter surface (80), enters the solid medium of the main lens (79), is reflected by the upper surface (81) towards the lower surface (83), where it is refracted again and exits the main lens (79). A light ray (87) originating in an additional scene (88), located at least partially above the cylindrical scene (86) is refracted by the central upper surface (82), penetrates the main lens (79), travels through the solid medium of the main lens (79) towards the lower surface (83), where it is refracted and exits the main lens (79). Light rays (89, 90) originating at an illumination source (91) travel through the illumination conductor (84), enter the main lens (79), are reflected by the upper surface (81) towards the perimeter surface (80) where they are refracted and exit the main lens (79), thus illuminating the cylindrical scene (86). Another light ray (92) originating at the same illumination source (91) takes a different optical path within the main lens (79) and is directed to illuminate the additional scene (88). To cause the light ray (92) to illuminate the additional scene (88), parts of the perimeter surface (80) can be coated with reflective material. Any such coating of the perimeter surface (80) does not compromise the coverage of the cylindrical scene (86), and is applied in an area (92), which is out of the range that covers that scene (86). All of the light rays discussed in the previous paragraph pass through the main lens (79) simultaneously, thus it is possible to image a nearly spherical scene, which comprises the cylindrical scene (86) and the additional scene (88), and at the same time to illuminate both scenes. Therefore, imaging of a nearly spherical scene is possible also in dark environments, for example in the inner canals of the body during medical endoscopy procedures, or in the interior of an engine.

Figure 13:
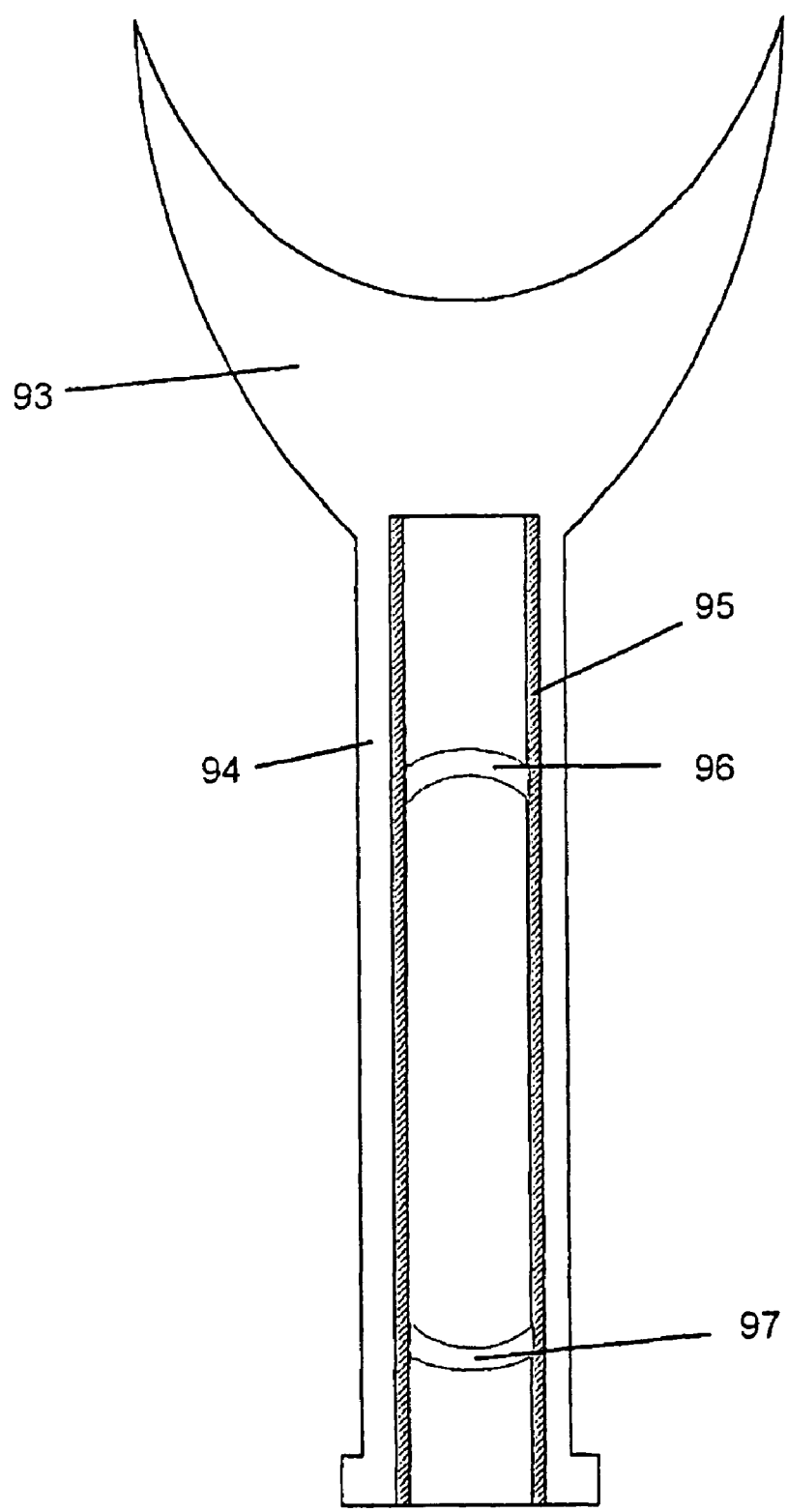
FIG. 13 shows schematically methods of combining additional components in the optical system that enable enhanced image quality and/or components that provide higher strength to the optical system.

In FIG. 13 is schematically shown an embodiment of the main lens that incorporates additional components in its holding element. In this embodiment, the main lens (93) is fabricated with, or connected to, a holding element (94), which can be also used as an illumination conductor as has been described hereinabove. The holding element is tube-shaped, therefore it is possible to insert inside it optical or mechanical components that will assist the overall performance of the optical system. For example, a blackened tube (95) may be inserted in contact with the inner wall of the holding element (95). The purpose of tube (95) is either to provide mechanical strength to the holding element (94) and/or to prevent glare that may be caused by light rays from the illumination source that exit through the transparent sides of the holding element (94). The tube (95) may also incorporate additional optical lenses (96,97), which are designed to enhance the quality of the image that exits the main lens (93).

Figure 14:
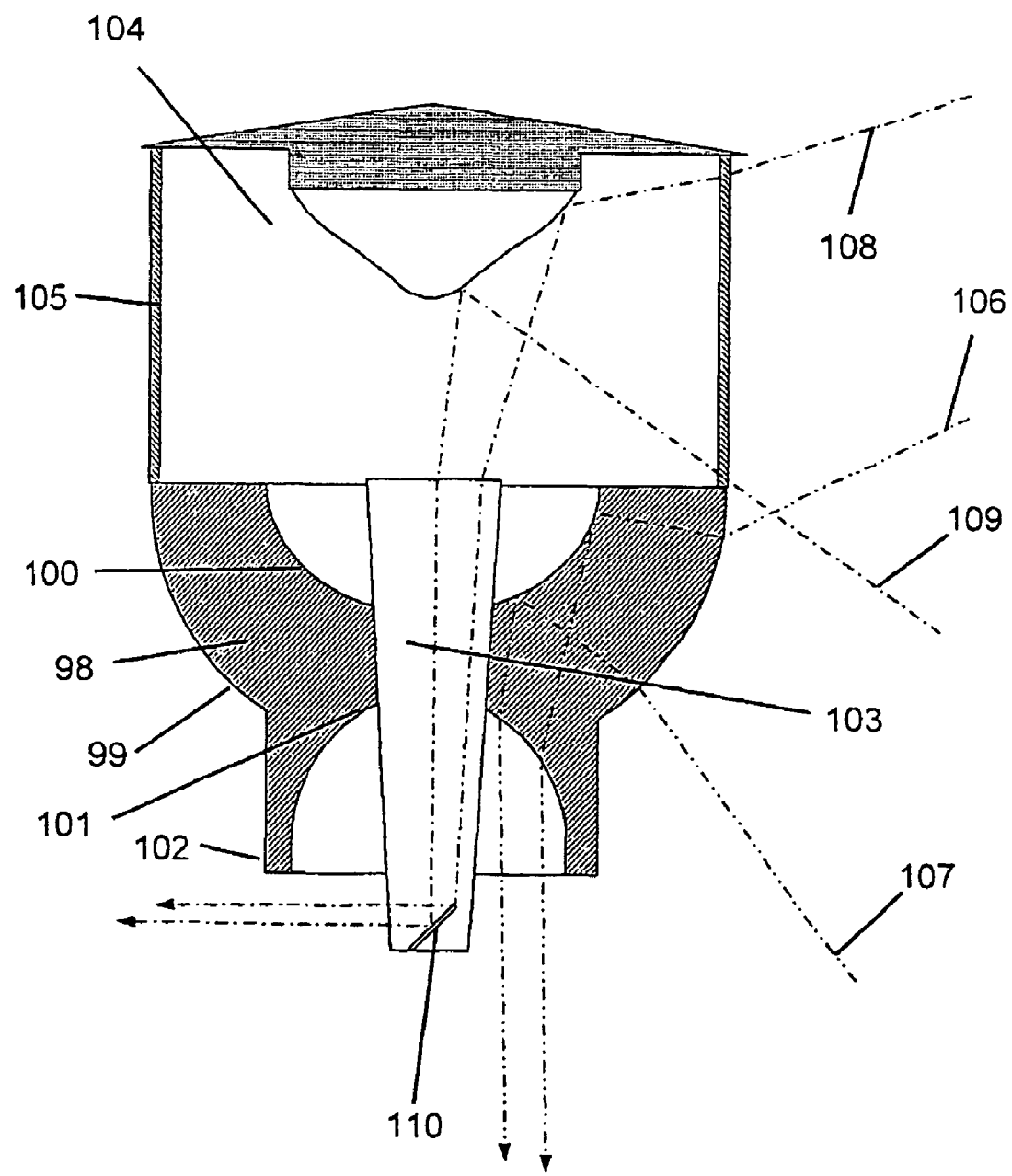
FIG. 14 shows schematically two omni-directional optical systems that enable imaging of the perimeter scene at two different wavelengths simultaneously.

In FIG. 14 is schematically shown an embodiment of the invention incorporating, in addition to the main lens, an additional optical lens that is also capable of covering at least a cylindrical field of view. This embodiment enables imaging of the perimeter scene at two different wavelengths. A first main lens (98) is made as a solid mold comprising a transparent perimeter surface (99), an upper transparent surface (100), preferably coated with reflective material from its exterior, a lower transparent surface (101) and a holding element (102). Additionally, the main lens (98) comprises a hole in its center, extending along its central axis of symmetry from its upper surface (100) to its lower surface (101). The hole is preferably conically shaped. Inside the hole there is placed an optical assembly (103). Coaxially with the main lens (98) and above it, there is placed an additional lens (104), which is capable of providing a reflection of at least the cylindrical scene around it. The additional lens (104) may be either a lens similar to one of the embodiments of the main lens described hereinabove or any axi-symmetric reflective surface or other type of suitable lens described in the prior art. The additional lens (104) is affixed to the main lens (98) with a suitable mechanical structure (105) that does not even minimally obscure the perimeter scene from the lens (104).

In the embodiment shown in FIG. 14, two image capture devices are used. A first image capture device (not shown) is designed to capture the image reflected by the main lens (98). A second image capture device (not shown) is designed to capture the image reflected by the additional lens (104). The two image capture devices are preferably sensitive to different wavelengths, compatible with the wavelength sensitivity of the lenses (98, 104). For example, the image capture device designed to capture the image reflected from the main lens (98) could be sensitive to the visible spectrum and the image capture device designed to capture the image reflected from the additional lens (104) could be sensitive to the near infra red spectrum. Those skilled in the art will understand that it is possible to control the wavelength sensitivity of the lenses (98, 104) by proper selection of the lenses material or the selection of the reflective coating used to coat the lenses.

A description of the optical paths of various light rays that travel through the system will now be given. A first group of light rays (106, 107) represent light rays that originate in the field of view covered by the main lens (98). These light rays (106, 107) are refracted by the perimeter surface (99), reflected by the upper surface (100) towards the lower surface (101) where they are refracted again and exit the main lens (98), and captured by a first image capture device (not shown) designed and set to capture the image that is reflected by the main lens (98).

A second group of light rays (108, 109) originating in the scene surrounding the additional lens (104), are refracted and reflected at the surfaces of the additional lens (104) and penetrate the optical assembly (103) located coaxially with additional lens (104). Inside the optical assembly (103) there is located at least a prism or reflective surface (110) designed to direct the rays reflected by the additional lens (104) to the second image capture device (not shown). As part of the optical assembly (103) there may be incorporated additional optical components that will enhance the quality of the image reflected by the additional lens (104).

It can therefore be seen that each of the two image capture devices acquires a different image. As previously stated, it is preferable that each image is in a different wavelength range. Thus it is possible to combine in the same system, two sub-systems that enable, for example, omni-directional imaging both in full lighting and in limited lighting conditions.

Proper optical design of the two lenses (98, 104) enables control over the vertical field of view of the cylindrical scene covered by each of the lenses.

Although embodiments of the invention have been described by way of illustration, it will be understood that the invention may be carried out with many variations, modifications, and adaptations, without departing from its spirit or exceeding the scope of the claims.

The invention claimed is:

1. A wide-angle imaging assembly comprising a main lens produced from an aspheric optical block, said aspheric optical block having:
   a. a vertical axis of symmetry;
   b. a transparent upper surface, at least part of which is capable of reflecting rays that impinge upon it from the inner side of said optical block;
   c. a transparent perimeter surface; and
   d. a transparent lower surface;
wherein the fabrication material of said optical block is selected to enable optical transmittance of a specific spectral range; and wherein light rays in the specific spectral range originating in a first scene having a 360 degrees panoramic perimeter are refracted by said transparent perimeter surface, enter said optical block, are then reflected by said upper surface towards said transparent lower surface, are then refracted by said transparent lower surface, and exit through said transparent lower surface;
said imaging assembly further comprising a transparent area fabricated as a hole in a part of the upper surface around the vertical axis of symmetry extending along the vertical axis of symmetry from the upper surface to the lower surface enabling light from a second scene, located at least partially above said first scene, to pass through said transparent area and travel through the optical block and exit said block.

2. A wide angle imaging assembly according to claim 1, wherein the shape of the hole is conical.

3. A wide-angle imaging assembly comprising a main lens produced from an aspheric optical block, said aspheric optical block having:
   a. a vertical axis of symmetry;
   b. a transparent upper surface, at least part of which is capable of reflecting rays that impinge upon it from the inner side of said optical block;
   c. a transparent perimeter surface; and
   d. a transparent lower surface;
wherein the fabrication material of said optical block is selected to enable optical transmittance of a specific spectral range; and wherein light rays in the specific spectral range originating in a first scene having a 360 degrees panoramic perimeter are refracted by said transparent perimeter surface, enter said optical block, are then reflected by said upper surface towards said transparent lower surface, are then refracted by said transparent lower surface, and exit through said transparent lower surface;
said imaging assembly further comprising:
   a. a hole which is conically shaped, extending along the vertical axis of symmetry from the upper surface to the lower surface; and
   b. a black cone compatibly shaped to be placed inside said hole,
wherein said cone is designed to prevent glare.

4. A wide-angle imaging assembly comprising a main lens produced from an aspheric optical block, said aspheric optical block having:
   a. a vertical axis of symmetry;
   b. a transparent upper surface, at least part of which is capable of reflecting rays that impinge upon it from the inner side of said optical block;
   c. a transparent perimeter surface; and
   d. a transparent lower surface;

wherein the fabrication material of said optical block is selected to enable optical transmittance of a specific spectral range; and wherein light rays in the specific spectral range originating in a first scene having a 360 degrees panoramic perimeter are refracted by said transparent perimeter surface, enter said optical block, are then reflected by said upper surface towards said transparent lower surface, are then refracted by said transparent lower surface, and exit through said transparent lower surface;

said imaging assembly further comprising a holding element, fabricated together with and a part of said optical block, said holding element located adjacent to the lower surface and extending downwards, wherein said holding element does not interfer with or block the rays that exit from said lower surface and a mechanical connector having a first edge and a second edge; where said first edge of said connector is designed to connect to said holding element and said second edge of said connector is designed to connect to an illumination source, positioning said illumination source adjacent to the exterior edge of said holding element.

5. A wide angle imaging assembly according to claim 4, further comprising an illumination source that distributes illumination rays, which travel through the holding element and are distributed by the surfaces of the optical block, wherein the wavelength of said illumination source is within the range of the specific spectral range to which said optical block is transparent.

6. A wide angle imaging assembly according to claim 5, comprising a plurality of illumination sources, capable of emitting more than one wavelength, wherein all of said illumination wavelengths are within the specific spectral range to which the optical block is transparent.

7. A wide-angle imaging assembly comprising a main lens produced from an aspheric optical block, said aspheric optical block having:
   a. a vertical axis of symmetry;
   b. a transparent upper surface, at least part of which is capable of reflecting rays that impinge upon it from the inner side of said optical block;
   c. a transparent perimeter surface; and
   d. a transparent lower surface;

wherein the fabrication material of said optical block is selected to enable optical transmittance of a specific spectral range; and wherein light rays in the specific spectral range originating in a first scene having a 360 degrees panoramic perimeter are refracted by said transparent perimeter surface, enter said optical block, are then reflected by said upper surface towards said transparent lower surface, are then refracted by said transparent lower surface, and exit through said transparent lower surface;

said wide-angle imaging assembly further comprising:
   a. an axi-symmetric lens, capable of refracting a second panoramic scene, which is at least partially included in the first scene; said axi-symmetric lens being positioned coaxially with and above the optical block;
   b. a hole extending along the vertical axis of symmetry of said optical block;
   c. an optical assembly located within said hole, said optical assembly comprising at least a prism or reflective surface designed to refract or reflect light rays that are reflected by said axis-symmetric lens; and
   d. a compatibly positioned image capture device, wherein said axi-symmetric lens is capable of transmitting light rays in a second spectral range which is at least partially different than the specific spectral range to which said optical block is transparent; said optical assembly does not interfere or block the rays reflected from said optical block; and said first panoramic scene provided by said optical block in said specific spectral range is at least partly identical to the panoramic scene provided by said axi-symmetric lens in said second spectral range.

* * * * *